(12) United States Patent
Sanjeeb et al.

(10) Patent No.: US 9,964,507 B2
(45) Date of Patent: May 8, 2018

(54) NOX GAS SENSOR INCLUDING NICKEL OXIDE

(71) Applicant: Honeywell International Inc., Morris Plains, NJ (US)

(72) Inventors: Tripathy Sanjeeb, Bangalore (IN); Abhilasha Srivastava, Bangalore (IN); Raju Raghurama, Bangalore (IN); Reddappa Reddy Kumbarageri, Bangalore (IN); Srinivas S. N. Mutukuri, Bangalore (IN)

(73) Assignee: Honeywell International Inc., Morris Plains, NJ (US)

( * ) Notice: Subject to any disclaimer, the term of this patent is extended or adjusted under 35 U.S.C. 154(b) by 53 days.

(21) Appl. No.: 15/171,758

(22) Filed: Jun. 2, 2016

(65) Prior Publication Data

US 2016/0282290 A1 Sep. 29, 2016

Related U.S. Application Data

(62) Division of application No. 13/407,453, filed on Feb. 28, 2012, now Pat. No. 9,389,212.

(Continued)

(51) Int. Cl.
*G01N 27/12* (2006.01)
*G01N 33/00* (2006.01)

(52) U.S. Cl.
CPC ......... *G01N 27/125* (2013.01); *G01N 27/127* (2013.01); *G01N 33/0037* (2013.01)

(58) Field of Classification Search
CPC ..................................................... G01N 27/16

(Continued)

(56) References Cited

U.S. PATENT DOCUMENTS 5,329,764 A * 7/1994 Hamburg ............ F02D 41/1441
  123/703
5,389,340 A * 2/1995 Satake ............... G01N 33/0037
  204/431

(Continued)

FOREIGN PATENT DOCUMENTS

WO 9934199 A1 7/1999

OTHER PUBLICATIONS

U.S. Appl. No. 13/407,453, First Office Action, dated Dec. 29, 2014, 8 pages.

(Continued)

*Primary Examiner* — Paul West
(74) *Attorney, Agent, or Firm* — Wick Phillips Gould & Martin LLP

(57) ABSTRACT

One example includes a sensor for sensing $NO_x$, including an electrically insulating substrate, a first electrode and a second electrode, each disposed onto the substrate, wherein each of the first electrode and the second electrode has a first end configured to receive a current and a second end and a sensor element formed of nickel oxide powder, the sensor element disposed on the substrate in electrical communication with the second ends of the first electrode and the second electrode. In some examples, electronics are used to measure the change in electrical resistance of a sensor in association with NOx concentration near the sensor. In some examples, the sensor is maintained at 575° C.

19 Claims, 10 Drawing Sheets

Related U.S. Application Data

(60) Provisional application No. 61/447,351, filed on Feb. 28, 2011.

(58) Field of Classification Search
USPC .............. 73/31.05, 31.06, 23.31–23.33
See application file for complete search history.

(56) References Cited

U.S. PATENT DOCUMENTS

| | | | | |
|---|---|---|---|---|
| 5,624,640 A | * | 4/1997 | Potthast | G01N 27/12 204/432 |
| 5,705,129 A | * | 1/1998 | Takahashi | G01N 33/0037 204/425 |
| 5,810,984 A | * | 9/1998 | Kudo | G01N 27/12 204/425 |
| 6,006,586 A | * | 12/1999 | Yoshida | G01N 33/0062 73/23.2 |
| 6,306,351 B1 | * | 10/2001 | Kudo | G01N 33/0037 204/426 |
| 6,968,679 B2 | * | 11/2005 | Pott | F02D 37/00 204/424 |
| 9,389,212 B2 | | 7/2016 | Sanjeeb et al. | |
| 2001/0035042 A1 | | 11/2001 | Moseley | |
| 2005/0016848 A1 | | 1/2005 | Sahimi et al. | |
| 2005/0093146 A1 | * | 5/2005 | Sakano | H01L 33/62 257/730 |
| 2008/0020504 A1 | * | 1/2008 | Raghurama | B82Y 30/00 438/48 |
| 2008/0128274 A1 | | 6/2008 | Raghurama et al. | |
| 2008/0169190 A1 | | 7/2008 | Raghurama et al. | |
| 2009/0020422 A1 | * | 1/2009 | A. | G01N 33/0037 204/406 |
| 2010/0096264 A1 | | 4/2010 | Nair et al. | |
| 2010/0106039 A1 | | 4/2010 | Abraham-Fuchs et al. | |
| 2011/0314899 A1 | * | 12/2011 | Di Miro | F02D 41/1466 73/23.33 |
| 2012/0161790 A1 | * | 6/2012 | Smith | G01N 27/125 324/658 |

OTHER PUBLICATIONS

U.S. Appl. No. 13/407,453, Second Office Action, dated Aug. 18, 2015, 9 pages.
U.S. Appl. No. 13/407,453, Notice of Allowance, dated Mar. 9, 2016, 8 pages.
U.S. Appl. No. 13/407,453, Restriction Requirement, dated Jul. 15, 2014, 7 pages.

* cited by examiner

NOX GAS SENSOR INCLUDING NICKEL OXIDE

CROSS REFERENCE TO RELATED APPLICATIONS

This application is a divisional of and claims priority benefit under 35 U.S.C. § 121 to co-pending U.S. patent application Ser. No. 13/407,453, filed Feb. 28, 2012, and entitled "NOX GAS SENSOR INCLUDING NICKEL OXIDE", which claims priority to U.S. Provisional Patent Application No. 61/447,351, filed Feb. 28, 2011, and entitled "NOX GAS SENSOR INCLUDING NICKEL OXIDE", which is related to U.S. Patent Application Publication No, 2008/0020504 and U.S. Patent Application Publication No. 2009/0020422, all of which are incorporated by reference herein in their entirety.

BACKGROUND

The generic term "NOx" describes oxides of nitrogen, such as nitrogen monoxide ("NO") and nitrogen dioxide ("$NO_2$"). NOx is produced as a by-product of combustion in some engines. Aircraft engines, automobile engines, and power generators, for example, utilize combustion processes that produce NOx.

NOx is believed to contribute to the production of acid rain, smog, and the depletion of the ozone layer. For example, reactions including volatile organic compounds and NOx, occurring in sunlight, are believed to form ozone. Ground-level ozone is believed to contribute to throat irritation, congestion, chest pains, nausea and labored breathing. Such ozone is believed to aggravate respiratory conditions like chronic lung and heart diseases, allergies and asthma. Ozone is believed to effectively "age" lungs and may contribute to lung disease. With an increase in the number of vehicles, the amount of NOx produced is increasing, and is believed to exacerbate environmental harm.

For at least these reasons, it is desirable to monitor NOx gas concentrations in emissions. In fact, NOx sensing, such as for emission control, is a requirement of regulations governing the operation of some diesel and spark ignition engines. Regions applying such regulations include countries in North America and Europe. As an example, in 2010, the total production of emission-regulated heavy-duty trucks, which will be required to monitor NOx, will be at least 1.5 million. Similar emission standards are being proposed for other internal combustion engines (i.e., passenger cars, boats, sport vehicles, etc.). Accordingly, there is a need for a reliable NOx sensor to monitor and control emissions.

DETAILED DESCRIPTION

In the following description, reference is made to the accompanying drawings that form a part hereof, and in which is shown by way of illustration specific embodiments that are practiced. These embodiments are described in sufficient detail to enable those skilled in the art to practice the embodiments, and it is to be understood that other embodiments are utilized and that structural, logical and electrical changes are made. The following description of example embodiments is, therefore, not to be taken in a limited sense, with the scope being defined by the appended claims.

NOx is sometimes estimated from measured NO, based on an assumption that total NOx is 5% $NO_2$ and 95% NO. This assumption is generally acceptable when combustion exhaust gases are measured at the outlet of the combustion system, and the oxygen concentration is low. If the measurement is made at the exhaust outlet or in the atmosphere, however, the $NO_2$ percentage is likely higher than 5% of the total NOx. For at least this reason, measurement of both NO and $NO_2$ is recommended for accurate total NOx concentration. Accordingly, the present subject matter provides sensors that measure both NO and $NO_2$, rather than deriving one measurement from the other.

The present subject matter provides several advantages. The sensors disclosed herein provide exemplary syntheses of NiO powder such as nanopowder capable of producing increasing conductivity (i.e., decreasing resistance measured at a sensor) in the presence of both NO and $NO_2$ gases. Various examples provide equal sensitivity to NO and $NO_2$, hence, reliable measurement of the total NOx content irrespective of the NO and $NO_2$ ratio. Examples disclosed herein provide fast response and recovery time (e.g., times less than 2 seconds for T66). Examples disclosed herein provide very low cross sensitivity (e.g., <2% of NOx sensitivity) to other gases present in the exhaust including, but not limited to, CO, $CO_2$, hydrocarbons, etc. Some examples provide nanomaterial that is nonreactive to poisonous gases present in the engine exhaust like $SO_2$ and silicone. Examples disclosed herein are robust and operate at high temperatures (e.g., at temperatures of around 550° C. to 575° C.). Some examples are packaged and are protected from contaminants like soot and hard particles present in the engine exhaust. Some examples are compatible with use directly in the engine exhaust stream. Various examples function stably in the various humidity levels (10% to 90%) in an atmosphere.

Certain examples include nickel oxide ("NiO") powder such as nanopowder synthesis showing change in conductivity to reducing NO gas and oxidizing $NO_2$ gas. Some examples demonstrate equal sensitivity to NO and $NO_2$ at an elevated working temperature of 550° C. to 575° C. Some examples are stable in corrosive and harsh environments such as those including $SO_2$, water vapor, high concentrations of $CO_2$, and combinations thereof.

Figure 1:
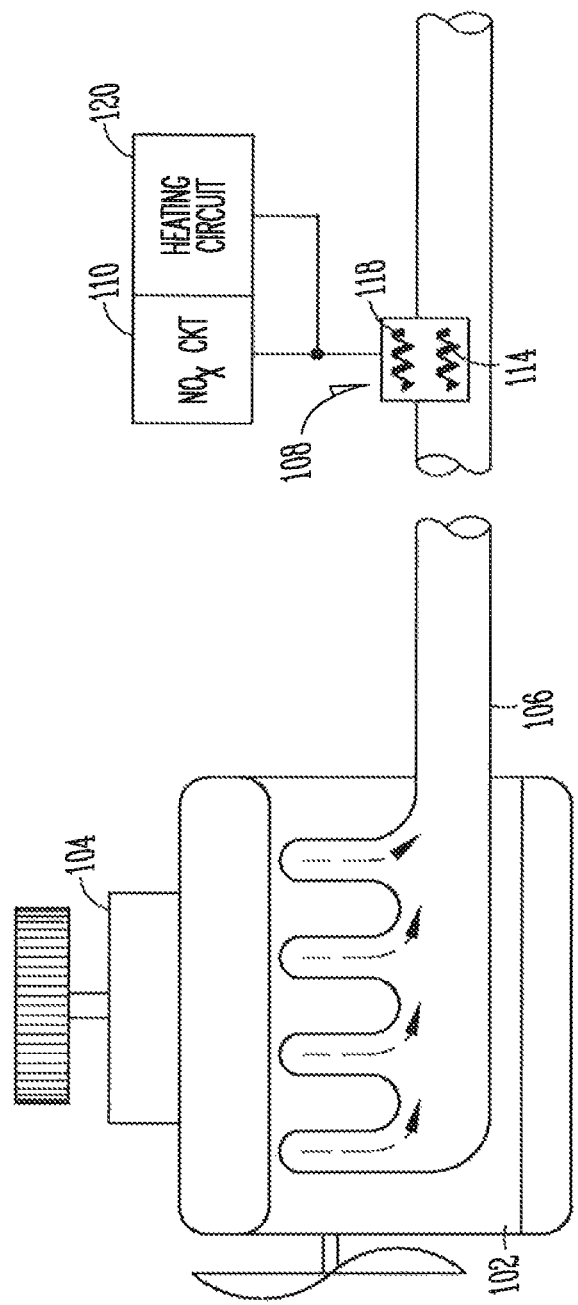
FIG. 1 illustrates an engine system including a sensor assembly coupled to an exhaust system, according to some examples.

FIG. 1 illustrates an engine system including a sensor assembly 108 coupled to an exhaust system 106, according to various examples. The engine system includes a combustion engine 102, such as a diesel engine, coupled to an intake system 104 and an exhaust system 106 to dispose of an exhaust stream of the combustion engine. A sensor assembly 108 is coupled to the exhaust system 106.

The sensor assembly 108 includes a NOx sensor 114 to sense the concentration of NOx in the exhaust stream of the exhaust system 106. Information associated with the changing NOx level is to inform one or more computers or engine operators how the engine is operating during engine calibration or engine operation. In some examples, NOx information is used as an input to one or more automatic controls used by an interconnected device, such as an engine controller, to control combustion. To monitor exhaust, some examples use a NOx sensing circuit 110 coupled to the sensor assembly 108 and NOx sensor 114 to detect a NOx indication produced by the NOx sensor 114 while the exhaust stream passes nearby the NOx sensor 114.

Although exhaust gases are heated while the system is in operation, in some examples, the sensor assembly 108 includes a heating element 118, controlled by the heating circuit 120, configured to heat the NOx sensor 114.

Figure 2:
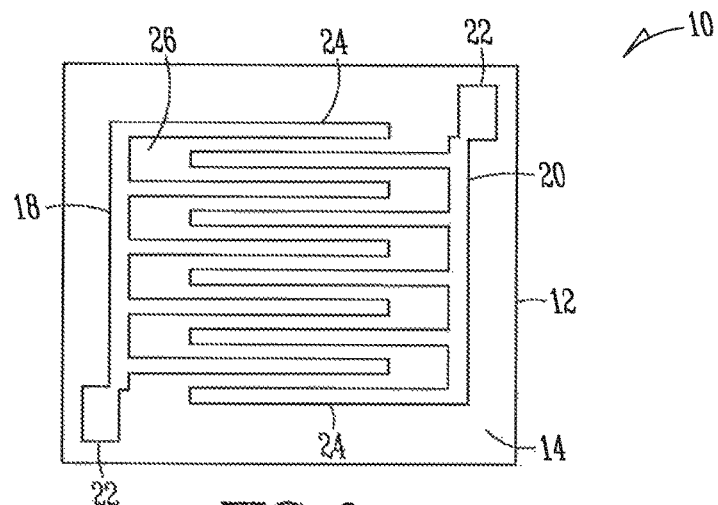
FIG. 2 is a top view of a nitrogen oxide sensor, according to some examples.
Figure 3:
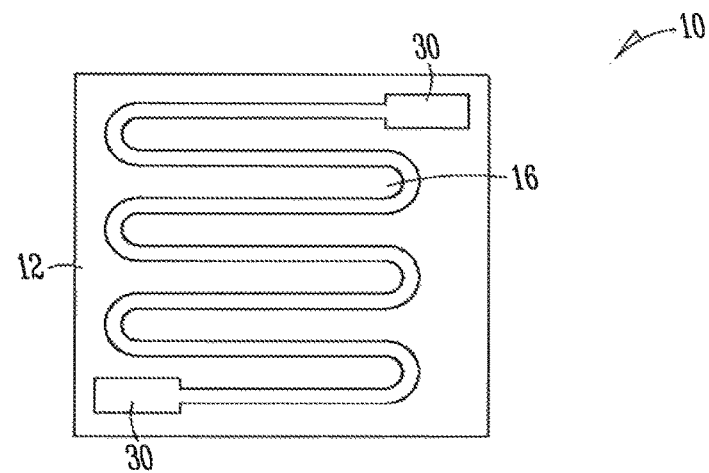
FIG. 3 is a bottom view of a nitrogen oxide sensor, according to some examples.
Figure 4:
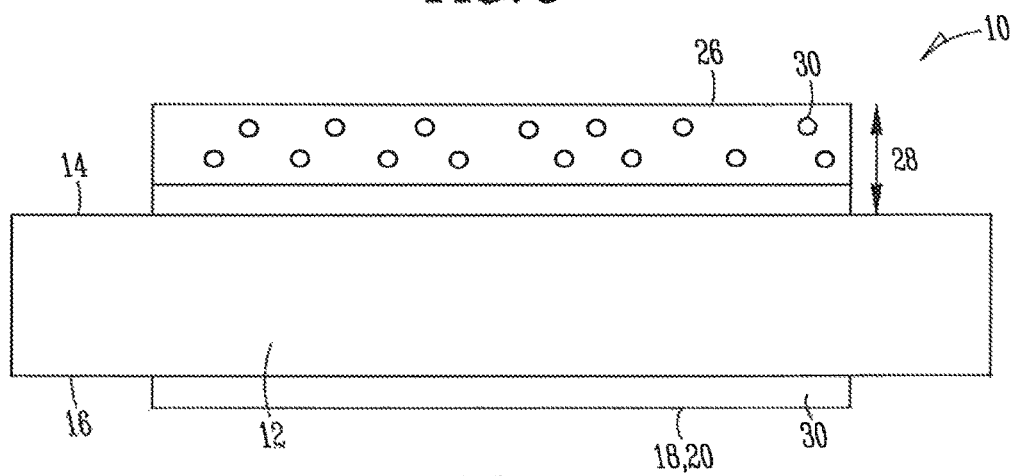
FIG. 4 is a side view of a nitrogen oxide sensor, according to some examples.

FIGS. 2-4 illustrate, according to some examples, a sensor 10 for detecting NOx. According to several examples, the sensor 10 comprises a substrate 12 having a first surface 14 and a second surface 16. In some examples, the second surface 16 is parallel to first surface 14. The substrate may be formed from any suitable electrically-insulating and heat resistant material such as, for example, a ceramic. In some examples, the substrate is formed of alumina ($Al_2O_3$). The substrate 12 may have any suitable size and shape. In some examples, the substrate 12 includes an elongated plate having a thickness in the range of about 0.5 millimeters (mm) to about 1 mm. In some examples, the substrate has a thickness of around 0.65 mm.

The sensor 10 includes a first electrode 18 and a second electrode 20 (e.g., inter-digital electrodes) disposed on the first surface 14 of the substrate 12. The electrodes may be formed of any suitable electrically conductive material. Examples of suitable materials from which the electrodes 18 and 20 are formed include, but are not limited to, platinum (Pt), gold (Au), nickel (Ni), silver (Ag), conducting metal oxides, and the like, including combinations thereof. Each of the electrodes 18 and 20 has a first end 22 and second ends 24. The first end 22 of each electrode is configured to receive a current. The second end 24 is configured in any suitable manner for conducting a current therebetween. In some examples, the second ends 24 of electrodes 18 and 20 are formed in an inter-digital structure, as illustrated in FIG. 2.

An element 26 including nickel oxide (NiO) is disposed in electrical contact with the second ends 24 of the electrodes 18 and 20. In some examples, the element 26 is disposed overlying the electrodes 18 and 20. In some examples, the element 26 is formed underlying the electrodes. In some examples, the second ends 24 of electrodes 18 and 20 are sandwiched between two elements 26. In some examples, the element 26 is sandwiched between the two electrodes. The element 26 is formed of any suitable nickel oxide material, including powder and nanopowder. In some examples, the element, is formed of nickel oxide. As illustrated in FIG. 4, the element 26 has a thickness, indicated by double-headed arrow 28. In some examples, the thickness 28 is in the range of about 120 microns In some examples, the sensor 10 comprises a heater 30 disposed on second surface 16 of the substrate 12. The heater 30 is comprised of any suitable heat-conducting material that is capable of heating the element 26 to a temperature of at least about 450° C. Possible materials include platinum (Pt), gold (Au), nickel (Ni), silver (Ag), conducting metal oxides, and the like, including combinations thereof. In some examples, the heater heats the element 26 to a temperature of at least 500° C. In some examples, the heater 30 is an elongated conductor formed of platinum.

The sensor 10, as described herein, has high sensitivity to NOx concentrations in a gas. Nickel oxide (NiO) is used as a NOx sensing element to sense NO and $NO_2$ or a mixture of NO and $NO_2$ (NOx), According to some examples, the NiO sensing element 26 acts as a catalyst to convert NO to $NO_2$. In some examples, the sensor 10 has improved efficacy when heated to a working temperature of from about 450° C. to about 575° C.

Without being bound by theory, the sensor experiences the resistance change at least because of $NO_2$ adsorption on the surface. In some examples, NiO powder such as nanopowder acting as a catalyst achieves sensitivity for both NO and $NO_2$ and a change in resistance in the same direction. In some examples, NiO powder such as nanopowder achieves changes in resistance for NO and $NO_2$ in opposite directions. Without being bound by theory, this is caused at least because NO is a reducing gas and $NO_2$ is an oxidizing gas. Such a response demonstrates that the sensor element is not converting NO to $NO_2$, according to some examples.

Figure 5A:
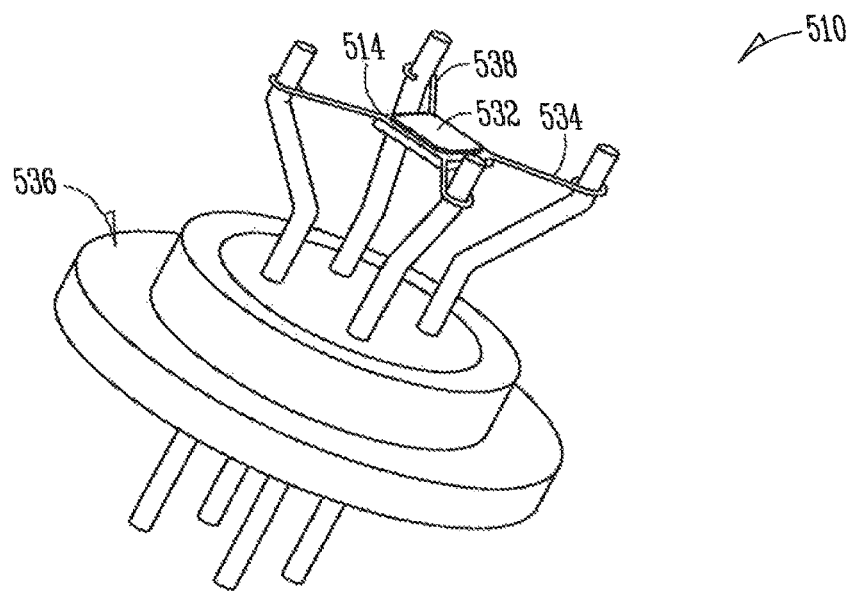
FIG. 5A is a partial perspective view of a sensor according to some examples.
Figure 5B:
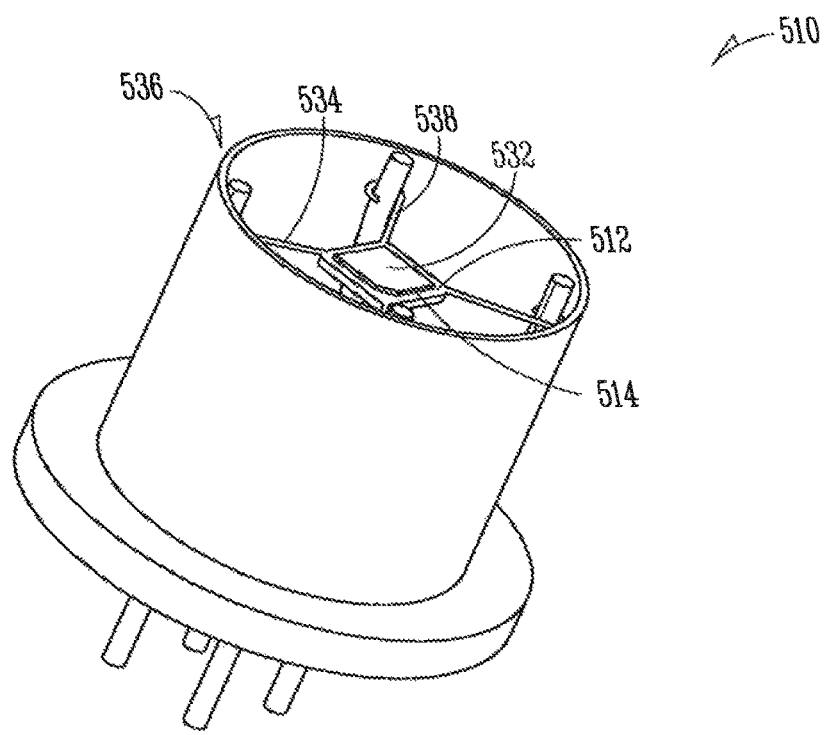
FIG. 5B is a partial perspective view of a sensor according to some examples.

FIG. 5A is a partial perspective view of a sensor according to some examples. FIG. 5B is a partial perspective view of a sensor according to some examples. According to several examples, the sensor 510 comprises a substrate 512 having a first surface 514 and a second surface, such as opposite the first surface. In some examples, the second surface is parallel to first surface 514. The substrate 512 is formed of any suitable electrically-insulating and heat resistant material such as, for example, a ceramic. In some examples, the substrate is formed of alumina ($Al_2O_3$). The substrate 512 may have any suitable size and shape. In some examples, the substrate 512 includes an elongated plate having a thickness in the range of about 0.5 millimeters (mm) to about 1 mm. In some examples, the substrate has a thickness of around 0.65 mm.

The sensor 510 includes a first electrode and a second electrode (e.g., inter-digital electrodes) disposed on the first surface 514 of the substrate 512. In certain examples, at least a portion of one or both of the first and second electrodes is potted with a potting material 532. Some examples include potting, such as with $Al_2O_3$, and bonding the sensor to wire 534. According to some examples, the sensor is packaged in a housing or housing assembly 536.

In some examples, the sensor 510 comprises a heater, such as a heater disposed on a second surface of the substrate, such as a second surface opposite the first surface 514. In some examples a wire 538 is coupled to the heater to power the heater.

Figure 6:
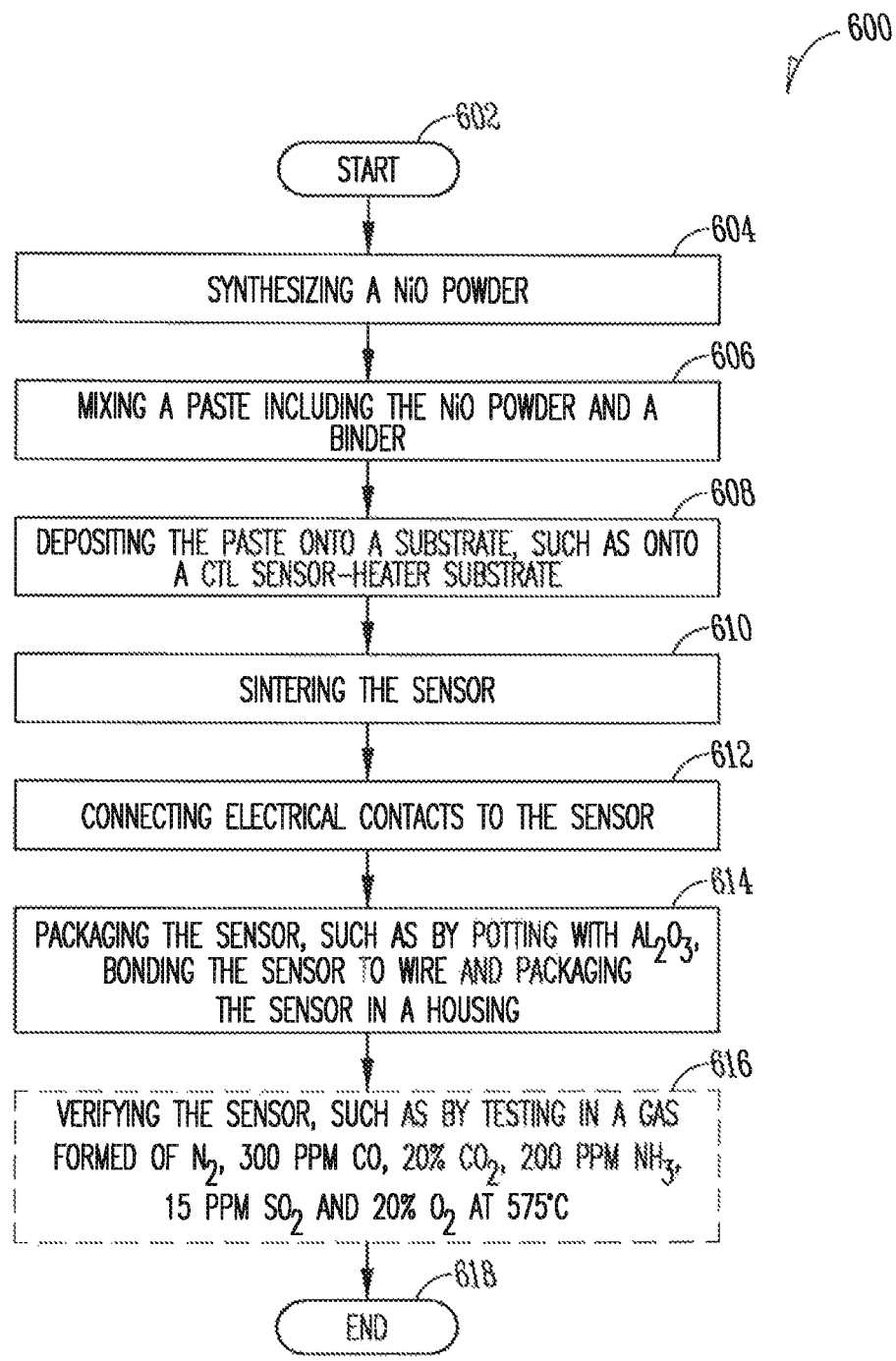
FIG. 6 is a flow chart of a method for fabricating a nitrogen oxide sensor, according to some examples.
Figure 7:
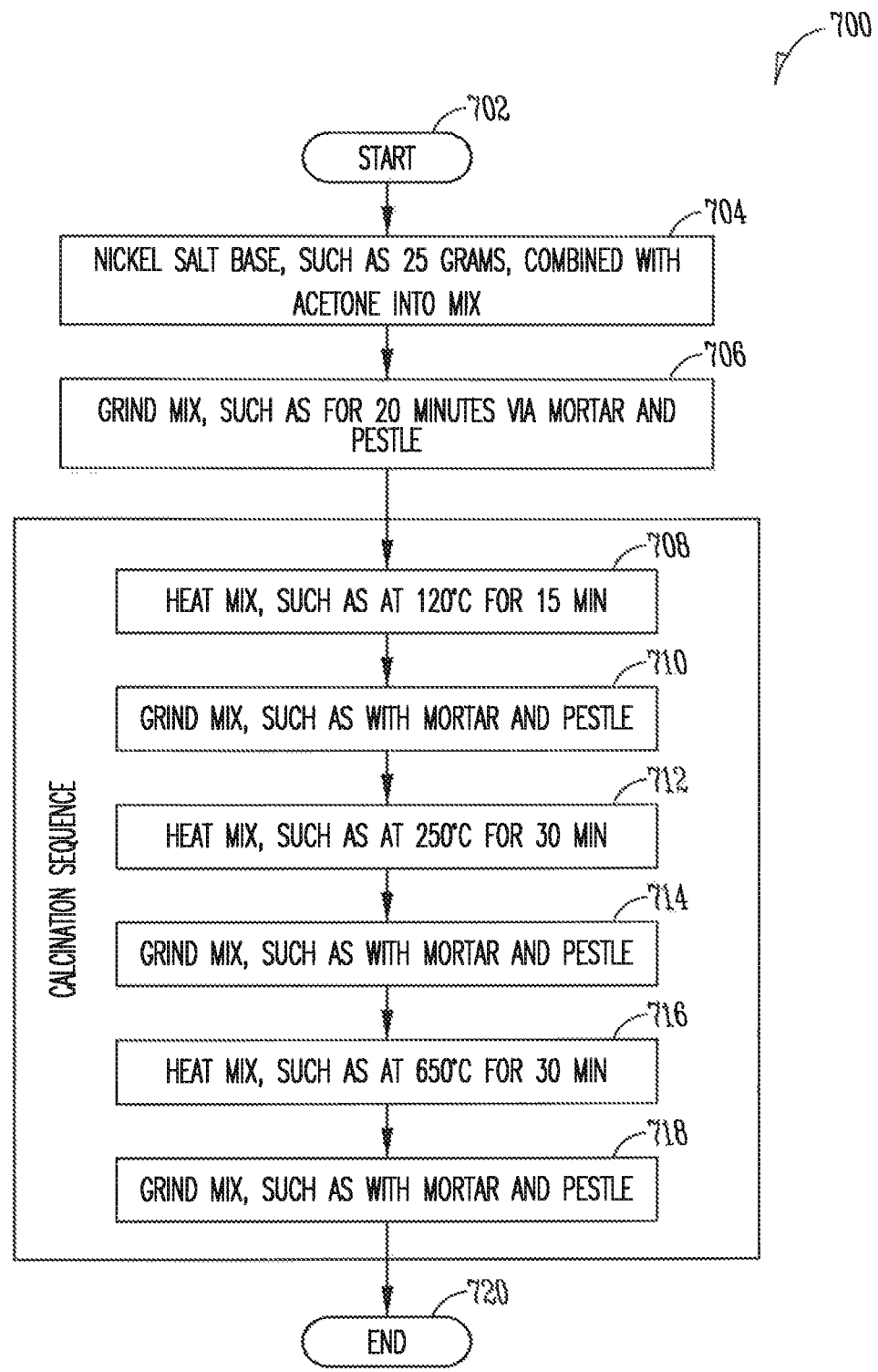
FIG. 7 is a flow chart of a method for synthesizing NiO powder such as nanopowder, according to some examples.
Figure 8:
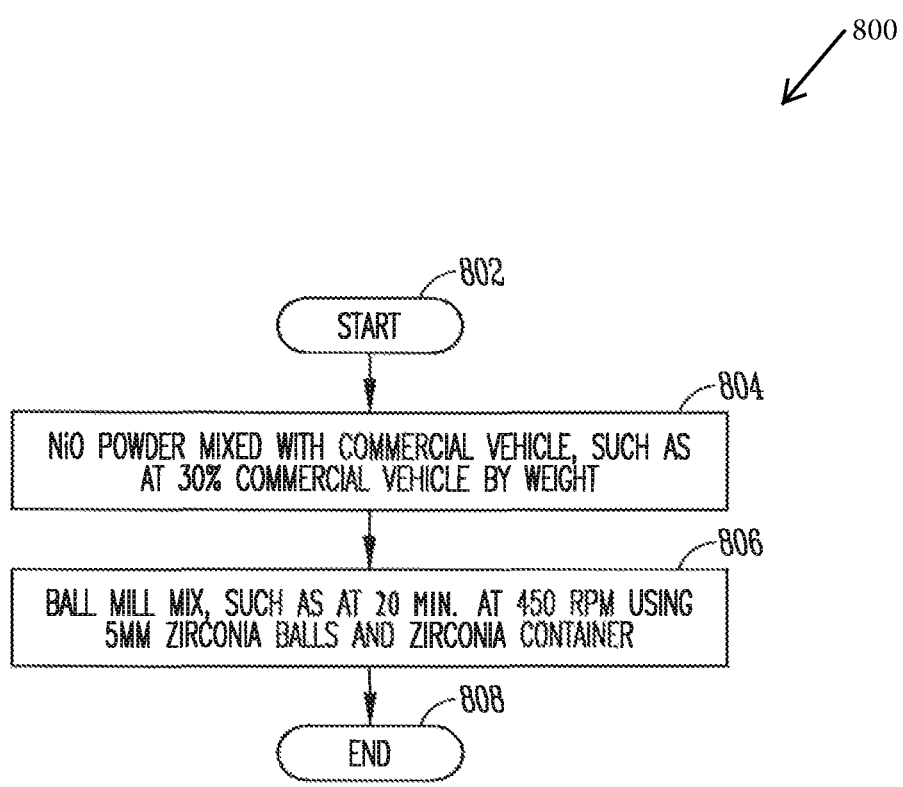
FIG. 8 is a flow chart of a method for mixing a paste including nickel oxide powder such as nanopowder, according to some examples.

FIG. 6 illustrates a method 600 for fabricating a sensor for detecting nitrogen oxides. The method starts at 602. At 604, the method includes a synthesis of NiO powder such as nanopowder. FIG. 7 describes an optional example of synthesis. At 606, the method includes mixing a paste including NiO powder such as nanopowder and a binder. FIG. 8 describes an optional example of mixing.

At 608, the method includes applying a paste onto a substrate, such as onto a CTL sensor-heater substrate or a Dietrich sensor-heater substrate. Some examples include providing an electrically-insulating and heat-resistant substrate plate having a first surface and a second surface. As described herein, the substrate can be formed from any suitable electrically-insulating and heat-resistant substrate such as, for example, alumina. Two electrodes of an electrically conductive material are formed on the first surface of the substrate, according to some examples. FIG. 8 describes an optional example application or deposition method in detail. According to some examples, the nickel oxide powder such as nanopowder is deposited as an element onto the first surface of the substrate in electrical contact with the second ends of the electrodes.

Some examples comprise forming a heater on the second surface of the substrate. In some examples, the heater is formed of the same material as the electrodes formed on the first surface of the substrate or is formed of any other suitable electrically conductive material such as, for example, platinum (Pt), gold (Au), silver (Ag), nickel (Ni), conducting polymers, conducting metal oxides, and the like, by any suitable method. In sonic examples, the heater is formed by combining a platinum paste with a suitable glass matrix and screen-printing the platinum paste/glass matrix mixture in a desired form onto the substrate. In some examples, the heater is then sintered, for example at about 1000° C. The heater can have any suitable form or structure conducive to heating the element to a temperature from about 400-700° C. Some examples heat to around 575° C.

Figure 10:
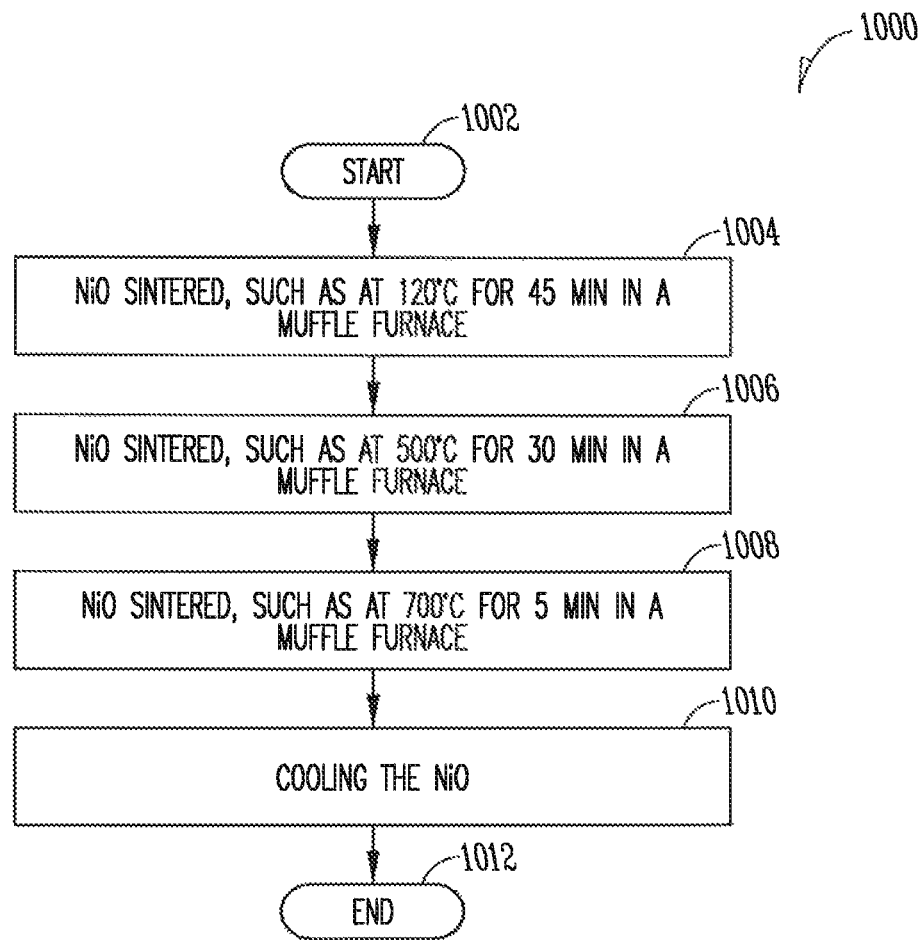
FIG. 10 is a flow chart of a method for sintering a sensor element, according to some examples.

At 610, the method includes sintering of the paste. As described above, the electrodes can have any suitable form or structure conducive to conducting a current therebetween. In some examples, the electrodes can have an elongated structure with inter-digital ends, as illustrated in FIG. 1. FIG. 10 describes an optional example sintering method in detail.

At 612, the method includes connecting electrical contacts to the sensor. The electrodes are formed of any suitable electrically conductive material such as, for example, platinum (Pt), gold (Au), nickel (Ni), silver (Ag), conducting metal oxides, and the like, by any suitable method. In some examples, the electrodes are formed by combining a platinum paste, ink, or paint with a suitable glass matrix and screen-printing the platinum paste/glass matrix mixture in a desired configuration onto the substrate.

In one example, the element is deposited overlying the second ends of the electrodes. In another example, the element is deposited on the substrate before the electrodes are formed on the substrate. In a further example, an element is deposited before the electrodes are formed on the substrate and is deposited overlying the second ends of the electrodes such that the electrodes are effectively "sandwiched" between two elements.

At 614, the method includes packaging the sensor, such as by potting with $Al_2O_3$ and bonding the sensor to wire and packaging the sensor in a housing. At 616, the process includes an optional method of verifying the sensor, such as by testing in a gas formed of $N_2$, 300 PPM CO, 20% $CO_2$, 200 PPM $NH_3$, 15 PPM $SO_2$, and 20% $O_2$, with the gas at 575° C. At 618, the process ends.

FIG. 7 is a flow chart of a method 700 for synthesizing NiO powder such as nanopowder, according to some examples. At 702, the process starts. At 704, the process includes combining nickel nitrate $Ni(NO_3)_2.6H_2O$ base, such as in the amount of 25 grams, combined with acetone into mix. The process and apparatus described herein are not limited to nickel nitrate, and other nickel salts, nickel nitrates, nickel acetates, nickel acetyl acetonates, nickel citrates and nickel tartrates both in hydrous and unhydrous form can be used to form the nickel oxide. Examples include, but are not limited to, $Ni(NO)_3.6H_2O$ (Nickel nitrate hexahydrate), $Ni(NO)_3$ (Nickel nitrate unhydrous), $Ni(C_2H_3O_2)_2$ (Nickel acetate), $C_{12}H_{10}Ni_3O_{14}$ (Nickel citrate), $(C_5H_7O_2)_2Ni.2H_2O$ (Nickel acetryl acetonate dihydrate), and combinations thereof.

At 706, the method includes grinding the mix, such as for 20 minutes via mortar and pestle. Some examples grind the mix for one hour. At 708, a calcination process begins. At 708 the process includes heating at 120° C. for around 15 minutes. At 710, the method includes grinding the powder such as nanopowder. At 712, the method includes heating at 250° C. for around 30 minutes. At 714, the method includes grinding the powder such as nanopowder. At 716, the method includes heating at 650° C. for around 30 minutes. At 718, the method includes grinding the powder such as nanopowder. At 720, the process ends.

FIG. 8 is a flow chart of a method 800 for mixing a paste including nickel oxide powder such as nanopowder, according to some examples. At 802, the process starts. At 804, the method includes mixing NiO powder such as nanopowder with commercial vehicle, such as at 30% commercial vehicle (for example ESL-3032-31) by weight. Examples of commercial vehicles include, but are not limited to, ESL 400, which is a Texanol-based paste product of ESL ElectroScience, King of Prussia, Pa. 19406-2625, At 806, the process includes ball milling the mix, such as for 20 minutes at 450 rpm forward and reverse using 5 mm zirconia (i.e., zirconium dioxide) balls and zirconia container. An example is a ball mill at 1 hour at 2400 rpm. At 808, the process ends.

Figure 9:
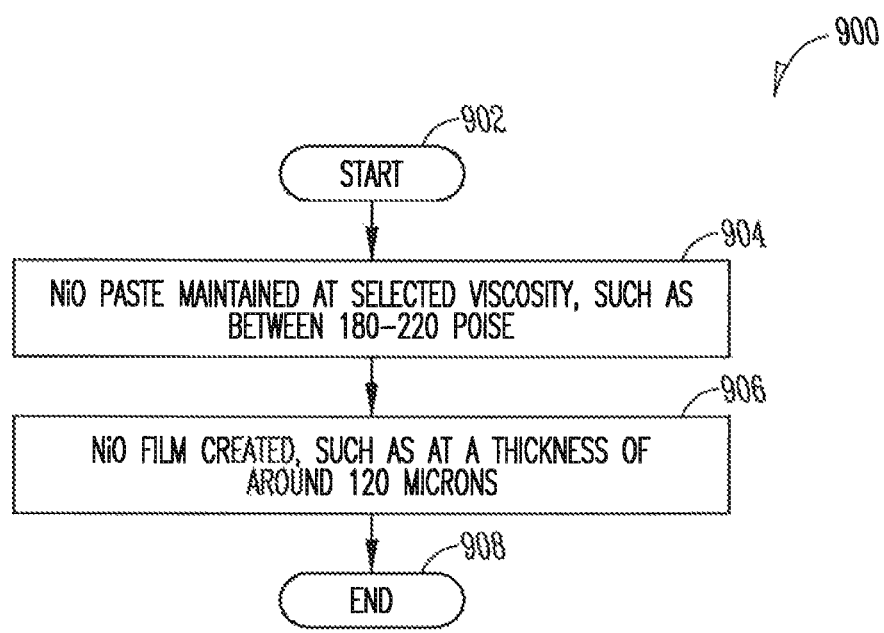
FIG. 9 is a flow chart of a method for applying a paste to a substrate, according to some examples.

FIG. 9 is a flow chart of a method 900 for applying a paste to a substrate, according to some examples. At 902, the process starts. At 904, the process includes maintaining the NiO paste at a selected viscosity, such as between 180-220 poise. At 906, the process includes creating a NiO film, such as at a thickness of around 120 microns. Creating such a film includes screen-printing, in some examples. In some examples, the powder such as nanopowder can be dispersed in an organic liquid such as, for example, hexane and deposited on the substrate by spin coating or dip coating or screen printing. It will be appreciated that any other suitable method for depositing the element on the substrate also is used. At 908, the process ends.

FIG. 10 is a flow chart of a method 1000 for sintering a sensor element, according to some examples. At 1002, the process starts. At 1004, the process includes sintering the NiO deposit, such as at 120° C. for 45 min in a muffle furnace. At 1006, the process includes sintering the NiO deposit, such as at 500° C. for 30 min in a muffle furnace. At 1008, the process includes sintering the NiO deposit, such as at 700° C. for 5 min in a muffle furnace. At 1010, the method includes cooling the NiO deposit. At 1012, the process ends.

Figure 11:
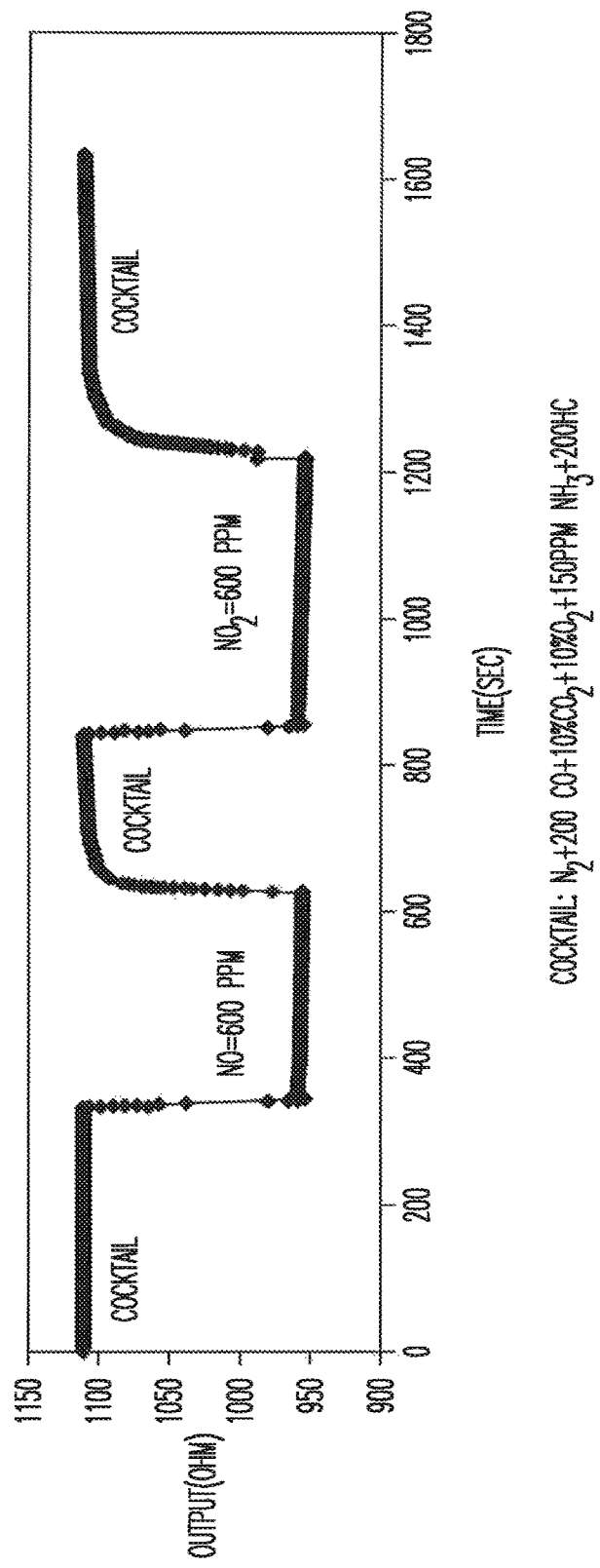
FIG. 11 shows the performance evaluation of the sensor by measuring the resistance change with gas concentration, and is made up of a nickel oxide sensor example, including nickel oxide powder such as nanopowder, exposed to cocktail gases at 575° C. showing sensitivity to NO and $NO_2$ according to some examples.

FIG. 11 is showing the response curves through resistance measurements of a nickel oxide sensor example, including nickel oxide powder such as nanopowder, exposed to cocktail gases at 575° C., showing sensitivity to NO and $NO_2$ according to some examples. The response curve shows a square-wave shaped response, with the high side associated with a cocktail of gasses with little or no NO or $NO_2$, and with the low side associated with the presence of one or both NO or $NO_2$ in an amount desired to be detected.

Figure 12:
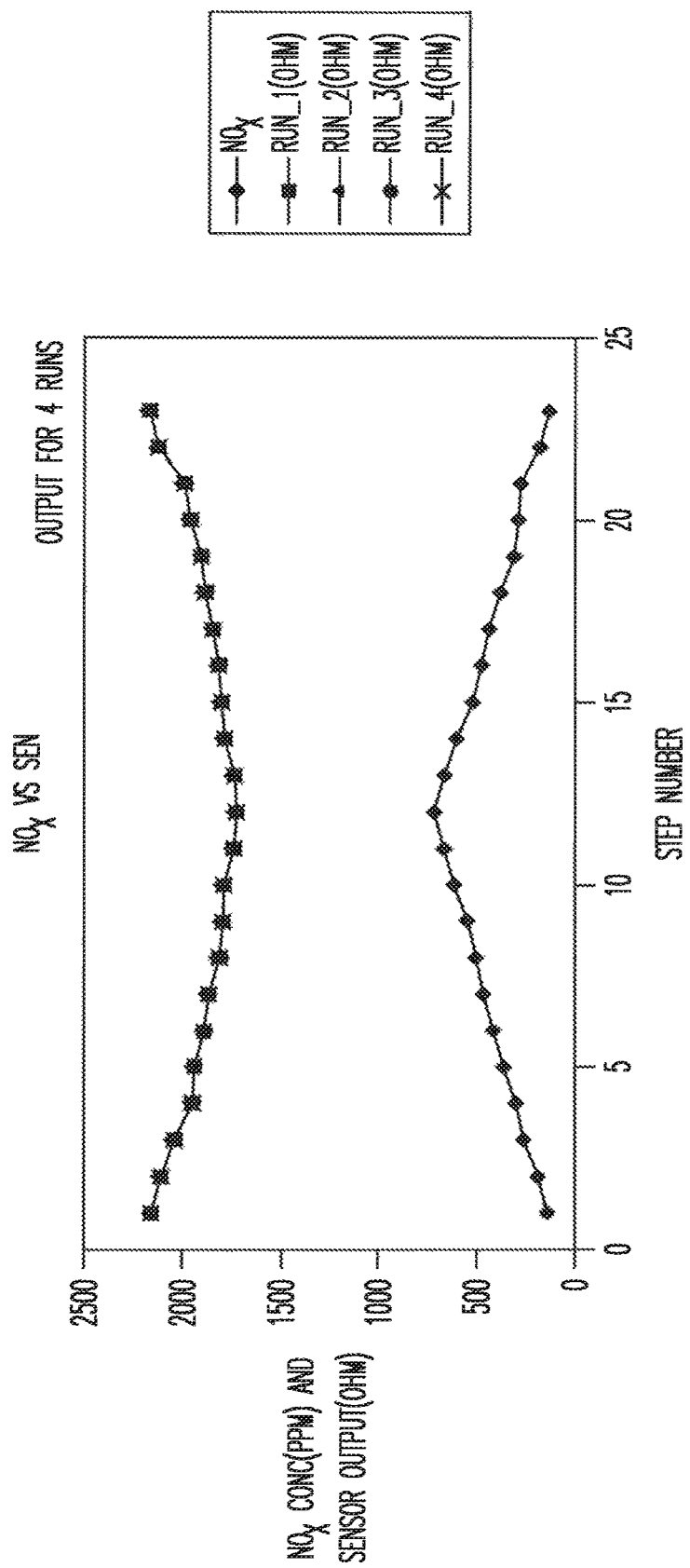
FIG. 12 shows the performance evaluation of the sensor by measuring the resistance change with gas concentration, and the engine response at different operational steps and sensor sensitivity to NOx, according to some examples.

FIG. 12 is showing sensor response in engine exhaust at different operational steps and sensor sensitivity to NOx, according to some examples. The step numbers are associated with different engine operating parameters, including, but not limited to, throttle position, fuel mixture, engine rpm, intake gas composition, and combinations thereof. In some examples, the step numbers are associated with increments in RPMs, such as increments of 100 rpm, but the present subject matter is not so limited. The response curve shows both that the sensor is able to detect the presence of NOx, and that sensor embodiments of the present disclosure are both accurate and precise.

Accordingly, NOx sensors and methods for forming such sensors have been provided. The sensors, according to some examples, are equally sensitive to NO and $NO_2$ gases in a gas and are insensitive to CO, $O_2$, $NH_3$, and hydrocarbon gases. In addition, the sensors provide fast response and are operable at high temperatures such as approximately 500° C. and higher.

The Abstract is provided to comply with 37 C.F.R. § 1.72(b) and is submitted with the understanding that it will not be used to interpret or limit the scope or meaning of the claims.

The invention claimed is:

1. An apparatus for sensing NOx, comprising:
   an electrically insulating substrate;
   a first electrode and a second electrode, each disposed onto the substrate, wherein each of the first electrode and the second electrode has a first end configured to receive a current and a second end;
   a sensor element formed of a sintered paste comprising nickel oxide powder, the sensor element disposed on the substrate in electrical communication with the second ends of the first electrode and the second electrode, wherein the nickel oxide powder comprises sintered powder formed of one or more of a group including nickel salts, organic salts of nickel, and inorganic salts of nickel; and
   a potting material, wherein at least a portion of the first electrode, the second electrode, or both are covered with the potting material.

2. The apparatus of claim 1, wherein the sensor element is disposed on a first surface of the substrate, opposite a second surface of the substrate, and further comprising a heater disposed on the second surface of the substrate, wherein the heater is configured to heat the sensor element to a temperature of at least about 500° C.

3. The apparatus of claim 1, wherein the powder includes a nanopowder.

4. The apparatus of claim 1, wherein the potting material comprises $Al_2O_3$.

5. The apparatus of claim 1, wherein 30% by weight of the sensor element comprises a vehicle.

6. The apparatus of claim 1, wherein the sensing element is around 120 microns in thickness.

7. An apparatus comprising:
   a sensor assembly comprising:
      a substrate;
      a first electrode and a second electrode, each coupled to the substrate, wherein each of the first electrode and the second electrode has a first end configured to receive a current and a second end; and
      a sensor element comprising nickel oxide, wherein the sensor element is disposed in electrical communication with the second ends of each of the first electrode and the second electrode, wherein the sensor element is configured to convert nitric oxide to nitrogen dioxide, wherein the sensor element is nonreactive to sulfur dioxide and silicone;
      and
   an engine system comprising:
      a combustion engine;
      an intake system coupled to the combustion engine,
      an exhaust system coupled to the combustion engine, wherein the sensor assembly is coupled to the exhaust system.

8. The apparatus of claim 7, wherein the substrate is formed from a ceramic.

9. The apparatus of claim 7, wherein the substrate is formed from alumina.

10. The apparatus of claim 7, wherein the first electrode and the second electrode are inter-digitated.

11. The apparatus of claim 7, wherein the first electrode and the second electrode are disposed between the sensor element and the substrate.

12. The apparatus of claim 7, wherein the sensor element is disposed on the substrate, and wherein the first electrode and the second electrode are disposed on the sensor element.

13. The apparatus of claim 7, wherein the sensor element is disposed on the substrate, and wherein the first electrode and the second electrode are embedded in the sensor element.

14. The apparatus of claim 7, wherein the sensor element is coupled to a first surface of the substrate, opposite a second surface of the substrate, and further comprising a. heater disposed on a second surface of the substrate.

15. The apparatus of claim 7, wherein at least one of the first electrode or the second electrode comprises: platinum (Pt), gold (Au), nickel (Ni), silver (Ag), a conducting metal oxide, or any combination thereof.

16. The apparatus of claim 7, wherein the sensor element is configured to provide an equal sensitivity to NO and NOx.

17. The apparatus of claim 7, wherein the sensor element has a cross sensitivity to gases other than NO and NOx of less than about 2% of a sensitivity to NOx.

18. The apparatus of claim 17, wherein the gases comprise CO, $CO_2$, a hydrocarbon, or any combination thereof.

19. The apparatus of claim 7, wherein the nickel oxide comprises a sintered nanopowder.

* * * * *

UNITED STATES PATENT AND TRADEMARK OFFICE
CERTIFICATE OF CORRECTION

PATENT NO. : 9,964,507 B2  
APPLICATION NO. : 15/171758  
DATED : May 8, 2018  
INVENTOR(S) : Tripathy Sanjeeb et al.

Page 1 of 1

It is certified that error appears in the above-identified patent and that said Letters Patent is hereby corrected as shown below:

On the Title Page

Item (74), Line 2: insert --,-- after "Martin"

Page (2), Item (56), U.S. PATENT DOCUMENTS, Line 8: "2001/0035042 A1 11/2001 Moseley" should be indented 3 spaces to the right In the Claims Column 8, Line 42: Claim 14 remove "." after "a"

Signed and Sealed this  
Twenty-first Day of August, 2018

Andrei Iancu  
*Director of the United States Patent and Trademark Office*